United States Patent [19]

Klesel et al.

[11] Patent Number: 5,350,753
[45] Date of Patent: Sep. 27, 1994

[54] PHARMACEUTICAL COMBINATION PREPARATIONS CONTAINING CEPHALOSPORIN AND XANTHINE DERIVATIVES AND THEIR USE

[75] Inventors: Norbert Klesel, Griesheim; Michael Limbert, Hofheim am Tauns, Fed. Rep. of Germany; Elmar Schrinner, Wiesbaden, all of Fed. Rep. of Germany

[73] Assignee: Hoechst Aktiengesellschaft, Frankfurt am Main, Fed. Rep. of Germany

[21] Appl. No.: 717,330

[22] Filed: Jun. 18, 1991

[30] Foreign Application Priority Data

Jun. 20, 1990 [DE] Fed. Rep. of Germany ....... 4019571

[51] Int. Cl.$^5$ ..................... A61K 31/52; A61K 31/545
[52] U.S. Cl. ...................................... 514/264; 514/202
[58] Field of Search ........................ 514/264, 210, 202

[56] References Cited

PUBLICATIONS

Muller, U. et al., Schweiz Med Wochenschr 116(43): 1495-7 1986.
Kwon, K. I. et al., J. Pharm Pharmacol 37(11): 836-9 1985.
Psychyrembel, Klinisches Wörterbuch Excerpt, p. 265. (1985).
Eufronio G. Maderazo et al. "Efficacy, Toxicity, and Pharmacokinetics of Pentoxifylline and Its Analogs in Experimental Staphylococcus Aureus Infections", Antimicrobial Agents and Chemotherapy, Jun. 1990, vol. 34, No. 6, pp. 1100–1106.

*Primary Examiner*—Marianne M. Cintins
*Assistant Examiner*—William R. A. Jarvis
*Attorney, Agent, or Firm*—Finnegan, Henderson, Farabow, Garrett & Dunner

[57] ABSTRACT

Pharmaceutical combination preparations containing cefotaxime and at least one xanthine derivative are suitable for the treatment of bacterial infectious diseases and for the treatment of septic shock.

6 Claims, No Drawings

PHARMACEUTICAL COMBINATION PREPARATIONS CONTAINING CEPHALOSPORIN AND XANTHINE DERIVATIVES AND THEIR USE

The present invention relates to pharmaceutical combination preparations containing cephalosporin and xanthine derivatives and their use for the prophylaxis and treatment of bacterial infectious diseases and for the treatment and prophylaxis of septic shock.

The antibiotic action of cephalosporins has been known for a long time. Different actions of xanthine derivatives are also known, inter alia also the TNF-inhibitory action of xanthine derivatives (EP 0,344,586) which allows the administration of xanthine derivatives to be indicated in the case of septic shock. Surprisingly, it has now been found that the activity of cephalosporin derivatives can be significantly increased by the simultaneous administration of xanthine derivatives.

The invention accordingly relates to pharmaceutical combination preparations which contain at least one cephalosporin derivative and at least one xanthine derivative.

The combination preparations according to the invention are suitable for the prophylaxis and treatment of bacterial infectious diseases and in particular for the prophylaxis and treatment of septic shock.

The preparation and the properties of cephalosporin derivatives are described, for example, in German Offenlegungsschriften 2,702,501, 2,713,272, 2,715,385, 2,810,922, 2,921,316, 2,922,036, in EP 0,064,740, and in GB 2,105,334 or GB 2,105,335. Physiologically tolerable salts of these compounds are also mentioned in said publications.

Preferred cephalosporin derivatives are those of the formula

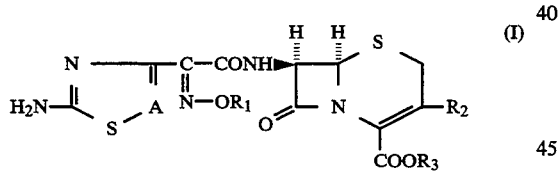

in which A is CH or N and $R_1$ can have the meaning of hydrogen, $C_1$-$C_4$-alkyl, carboxy-$C_1$-$C_4$-alkyl or a group of the formula

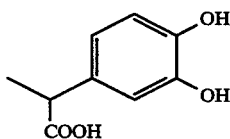

and in which the group =N—$OR_1$ is in the syn-position, $R_2$ can have the meaning of hydrogen, methyl, methoxy, vinyl, acetoxymethyl, carbamoyloxymethyl, of

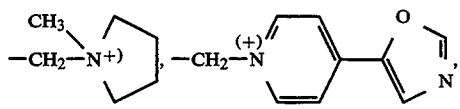

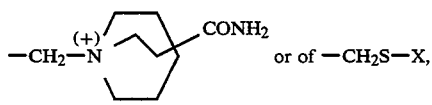

or of —$CH_2$S—X,

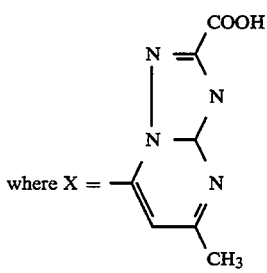

where X =

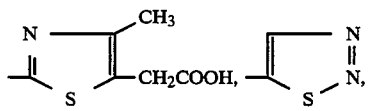

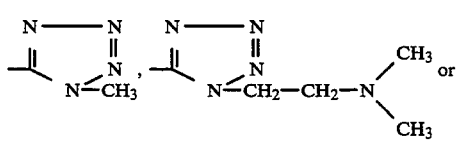

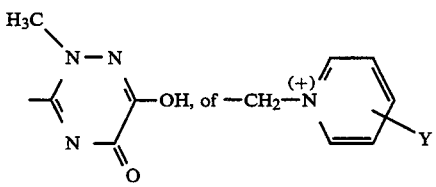

where Y = hydrogen,
$C_1$-$C_4$-alkylthio,
$C_1$-$C_4$-alkoxy or
$C_3$-$C_5$-cycloalkyl,

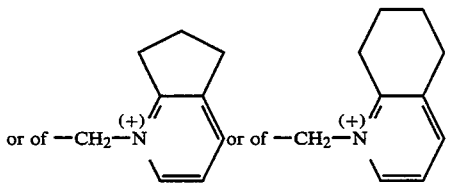

where the fused rings are also in the 3,4-position and can also be interrupted by oxygen, of

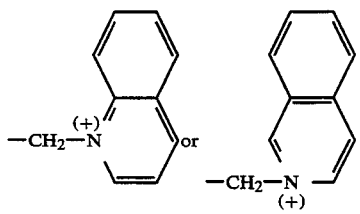

of thienopyridiniomethyl, furopyridiniomethyl or of 5-methyltetrazol-2-yl-methyl and $R_3$ can be hydrogen, a physiologically tolerable cation, a physiologically tolerable ester radical or—if the structure

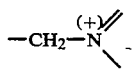

occurs in $R_2$—a negative charge.

In the formula I A is preferably CH.

If $R_1$ is $C_1$–$C_4$-alkyl, suitable radicals are, for example, methyl, ethyl or propyl preferably methyl.

If $R_1$ is carboxy-$C_1$–$C_4$-alkyl, carboxymethyl, carboxyethyl or carboxypropyl, for example, preferably the radical —$CH_2$—COOH, but in particular the radical

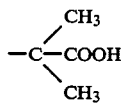

are of interest.

Of the substituted pyridinium-methyl radicals mentioned above, 2,3-cyclopenteno- and 2,5-cyclohexeno-pyridinium-methyl, and 4-methylthio-, 4-cyclopropyl- and 3-methoxy-pyridinium-methyl, and also 3,4-cyclopenteno- and 3,4-cyclohexeno-pyridinium-methyl are preferred.

Of very particular interest according to the invention are those compounds of the formula I in which $R_1$ is methyl and $R_2$ is —$CH_2$—$OCOCH_3$ (cefotaxime),

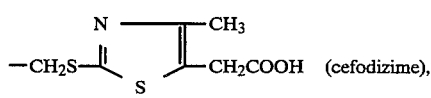 (cefodizime),

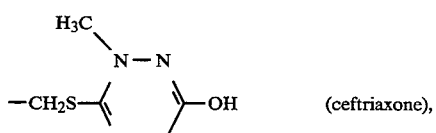 (ceftriaxone),

 (cefmenoxime) or

 (cefpirome), or $R_1$ is —$CH_2COOH$ and $R_2$ is —$CH$=$CH_2$ (cefixime), cefodizime, cefpirome, cefotaxime and ceftriaxone again assuming a preferential position within this group.

If $R_2$ is a —$CH_2$—pyridinium compound, the carboxyl group in the general formula I is present as the anion of an internal salt (—$COO^{(-)}$).

$R_3$ can be hydrogen or a physiologically tolerable cation, such as, for example, an alkali metal cation, preferably potassium or sodium, in particular sodium, or also other physiologically tolerable cations known from the literature, such as, for example, alkaline earth metal or organic ammonium ions (cf., for example, U.S. Pat. No. 4,278,793).

$R_3$ may furthermore be a physiologically tolerable ester radical which is in particular of interest for enteral administration, such as, for example, an acyloxymethyl or acyloxyethyl radical having 2 to 12, preferably 2 to 6, carbon atoms in the acyl moiety, preferably acetoxymethyl, 1'-(acetoxy)ethyl or pivaloyloxymethyl, 5-methyl-1,3-dioxalen-2-on-4-yl methyl, or, alternatively, other physiologically tolerable ester radicals, as are described, for example, in EP-A 0,170,028.

Among the aminothiazole cephalosporins which contain —$CH_2$— instead of —$C(=N$—$OR_1)$—, cefotiam and among the N-acylphenylglycine cephalosporins, cefoperazone (cf., for example, EP-0,248,361) may be further mentioned as particularly interesting cephalosporin derivatives.

Further examples of preferred cephalosporin derivatives according to the invention are selected from the group comprising the following compounds:

cefpirome, a compound of the formula

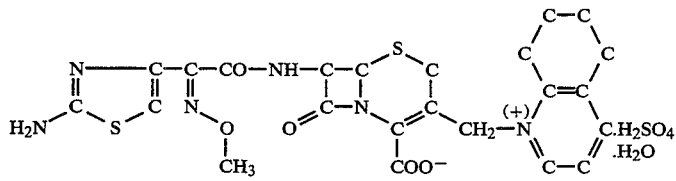

cefuroxime, a compound of the formula

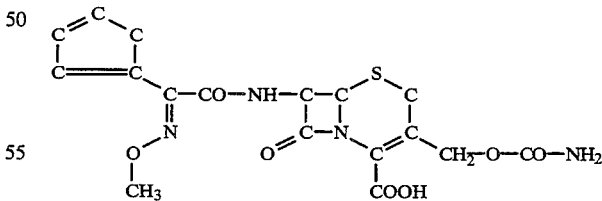

ceftizoxime, a compound of the formula

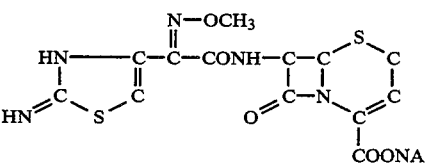

and ceftazidime, a compound of the formula omethyl]-8-oxo-5-thia-1-azabicyclo [4.2.0 ]oct-2 -ene-2 -carboxylic acid,
a compound of the formula

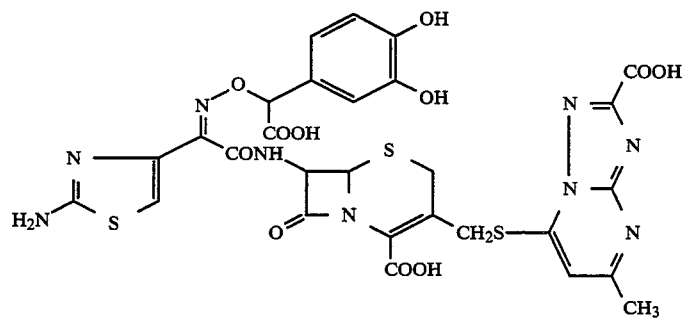

(6R,7R)-7-[(5-amino-1,2,4-thiadiazol-3-yl)-(Z)-methoxyiminoacetamido]-3-[4-carbamoyl -1-quinuclidiniomethyl ]-8-oxo-5-thia-1-azabicyclo[4.2.0]oct-2 -ene-2 -carboxylate,
a compound of the formula

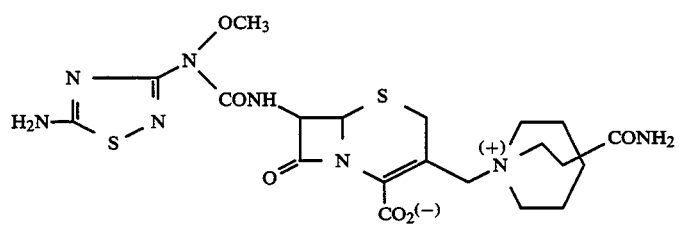

and their physiologically tolerable salts or esters.

A very particularly preferred cephalosporin derivative is cefotaxime (Claforan ®, Hoechst AG, Frankfurt).

Preferred xanthine derivatives to be used according to the invention are derived from the group comprising the following compounds:

1) compounds of the formula I

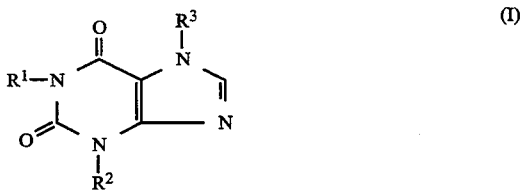

in which one of the radicals $R^1$ and $R^3$ is a straight-chain alkyl, ($\omega$-1)-oxoalkyl or ($\omega$-1)-hydroxyalkyl group having 3 to 8 carbon atoms and the two other radicals $R^2$ and $R^3$ or $R^1$ and $R^2$ are straight-chain or branched alkyl groups having 1 to 8 carbon atoms in the position of $R^1$ and $R^3$ and 1 to 4 carbon atoms in the position of $R^2$, the sum of the carbon atoms of these two alkyl substituents being at most 10, 2) compounds of the formula II Further particularly preferred cephalosporin derivatives are selected from the group comprising the following compounds:

cefepime, a compound of the formula

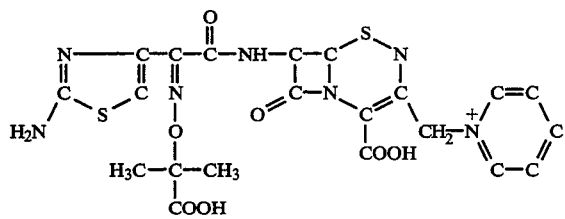

7-[(2-amino-thiazol-4-yl)-methoxyimino-acetamido]-3-[4-(oxazol- 5-yl )-1-pyrimidiniomethyl]-8-oxo-5-thia-1-azabicyclo-[4.2.0]oct-2-ene-2-carboxylate, a compound of the formula

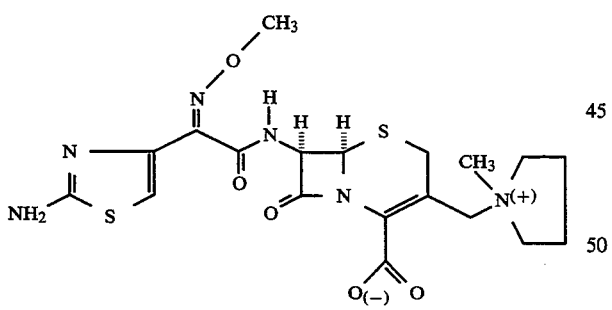

(6R, 7R)-7-[(2-amino-thiazol-4-yl)-((Z)-(S)-α-carboxy-3,4-dihydroxy-benzyloxyimino) -acetamido ]-3- [(2-carboxy-5-methyl-S-triazolo [1,5-a ]-pyrimidin-7-yl )-thi-

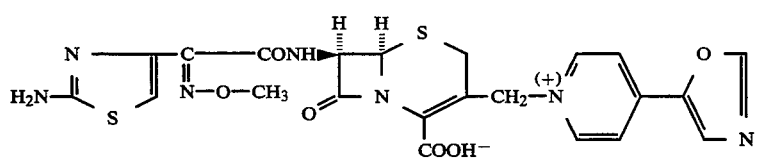

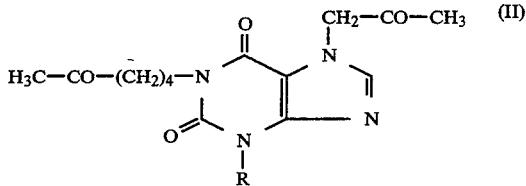

in which R is an alkyl radical having 1 to 4 carbon atoms, 3) compounds of the formula III

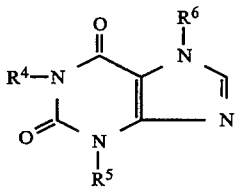

in which at least one of the radicals $R^4$ and $R^6$ is a tertiary hydroxyalkyl group of the formula

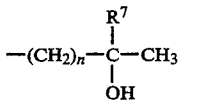

where $R^7$ is an alkyl group having up to 3 carbon atoms and n is an integer from 2 to 5, and—if only one of the radicals $R^4$ or $R^6$ is such a tertiary hydroxyalkyl group of the formula IIIa—the other radical is a hydrogen atom or an aliphatic hydrocarbon radical $R^8$ having up to 6 carbon atoms whose carbon chain can be interrupted by up to 2 oxygen atoms or can be substituted by an oxo group or up to two hydroxyl groups (where an oxo or hydroxyl group located in the radical $R^8$ is preferably separated from the nitrogen by at least 2 carbon atoms), and $R^5$ is an alkyl group having 1 to 4 carbon atoms, 4) prodrug forms of the compounds of the formulae I to III and/or 5) metabolites of the compounds of the formulae I to III.

Among these compounds, in turn, those of the formula I are particularly preferred which carry a hexyl, 5-oxohexyl or 5-hydroxyhexyl group in the $R^1$ or $R^3$ position.

These in particular include
1-hexyl-3,7-dimethylxanthine,
1-(5-hydroxyhexyl)-3,7-dimethylxanthine,
3,7-(dimethyl-1-(5-oxohexyl)-xanthine,
7-(5-hydroxyhexyl)-1,3-dimethylxanthine,
1,3-dimethyl-7-(5-oxohexyl)-xanthine,
1,3-di-n-butyl-7-(2-oxopropyl)-xanthine,
1,3-di-n-butyl-7-(3-oxobutyl)-xanthine,
1-(5-hydroxyhexyl)-3-methyl-7-propylxanthine and
3-methyl-1-(5-oxohexyl)-7-propylxanthine
(=propentofylline), in particular
3,7-dimethyl-1-(5-oxohexyl)-xanthine
(=pentoxifylline).

Further particularly preferred compounds of the formula III are those compounds in which $R^5$ is a methyl or ethyl group. Equally preferred are those compounds of the formula III in which only one of the two radicals $R^4$ or $R^6$ is the tertiary hydroxyalkyl group defined above. Additionally preferred are those compounds in which $R^7$ is a methyl group and n is an integer from 3 to 5, so that the tertiary hydroxyalkyl radical IIIa is either [(ω-1)-hydroxy-(ω-1)-methyl]-pentyl, -hexyl or -heptyl, in particular those in which $R^5$ is methyl or ethyl.

Those compounds of the formula III are additionally to be particularly emphasized in which $R^4$ is the tertiary hydroxyalkyl group and $R^6$ is hydrogen, alkyl, hydroxyalkyl or alkoxyalkyl in each case having 1 to 4 carbon atoms, such as, for example, 7-propyl- or 7-ethoxymethyl-1-(5-hydroxy-5-methylhexyl) - 3-methylxanthine and 1-( 5-hydroxy-5-methylhexyl)-3-methylxanthine.

1-( 5-Hydroxy-5-methylhexyl) -3-methylxanthine is very particularly preferred.

A further embodiment of the invention consists in not employing the oxoalkylxanthines of the formulae I and II or the hydroxyalkylxanthines of the formulae I and III per se, but in prodrug form from which the therapeutically active xanthine compounds having the substituents defined in formulae I, II and III can only be released by biotransformation in the organism. Suitable compounds for this purpose are, for example, the acetalized oxoalkylxanthines in which the carbonyl groups are replaced by the structural element of the formula IV

and the O-acylated hydroxyalkylxanthines having the structural element of the formula (V)

instead of the hydroxyl function, where $R^9$ and $R^{10}$ in each case are an alkyl group having up to 4 carbon atoms or together are an ethylene, trimethylene or tetramethylene group and $R^{11}$ is an alkyl radical having up to 4 carbon atoms, or optionally substituted phenyl or pyridyl.

The preparation of xanthine derivatives is described, for example, in DE-B-1,233,405, DE-B-1,235,320 or DE 3,525,801A1.

The cephalosporin derivatives can be administered both in combination with the xanthine derivatives in separate dosage units (at the same time or in succession) and mixed with the xanthine derivatives.

The production of pharmaceutical combination preparations according to the invention, to which the present invention also relates, is carried out by bringing at least one cephalosporin derivative and at least one xanthine derivative into a suitable administration form, if appropriate using further additives and/or auxiliaries. The additives or auxiliaries are derived from the group comprising the excipients, preservatives and other customary auxiliaries. For example, for oral administration forms auxiliaries such as starch, for example potato, maize or wheat starch, cellulose or its derivatives, in particular microcrystalline cellulose, silica, various sugars such as lactose, magnesium carbonate and/or calcium phosphates can be used. It is furthermore advantageous to add auxiliaries to the oral administration forms which improve the tolerability of the medicaments, such as, for example, mucus-forming agents and resins.

For better tolerability, the medicaments can also be administered in the form of gastric juice-insoluble capsules. Moreover, it may be advantageous to add a sustained release agent, if appropriate in the form of permeable membranes, such as, for example, those based on cellulose or polystyrene resin, or ion exchangers to the administration form or to a component of the combination preparation.

Said pharmaceutical combination preparations can be administered in various ways. For example, they can be administered intravenously, intramuscularly, intraperitoneally, subcutaneously or orally.

The ratio of the cephalosporin derivatives to the xanthine derivatives in the pharmaceutical combination preparations according to the invention can extend over a wide range. A weight ratio of about 1:100 to about 100:1, particularly preferably of about 1:10 to about 10:1, is to be preferred.

In the example which follows, the increase in the antibacterial activity of cefotaxime as a result of combination with 1-(5-hydroxy-5-methylhexyl)-methylxanthine (HMHM) is investigated.

EXAMPLE 1

NMRI mice having an experimental weight of 10–22 g are used as experimental animals. The animals have access to tap water and granulated feed ad libitum during the experiments.

The three bacterial strains *Staphylococcus aureus* Giorgio, *Escherichia coli* 078 and *Salmonella typhimurium* MZ II used in this study showed a high infectiousness in preliminary experiments with mice. Suspensions of these infective agents (in 15% skimmed milk as freeze protection) are stored in liquid nitrogen. Before the experiments, the suspensions are adjusted to the multiple lethal infectious doses (in colony-forming units, CFU) in 5% strength mucin. They are $1 \times 10^6$ CFU per mouse in the case of infection with *S. aureus* Giorgio, $1 \times 10^4$ CFU per mouse in the case of *E. coli* 078 septicemia and $2.5 \times 10^3$ CFU per mouse in the case of *S. typhimurium* MZ II infection.

The mice are infected intraperitoneally with 0.3 ml of suspension of the three bacterial strains in 5% pig gastric mucin.

The infectious dose contains, according to the microorganism, a 10 to 500-fold lethal dose of bacteria. Depending on the infectire agent, the infected animals of the untreated control group die within six to 24 hours after establishing the infection.

A group of eight infected animals is used as the infection control. The animals receive 0.5 ml of physiological saline solution immediately after establishing the infection.

A second group of eight infected animals is treated with 50 mg/kg of HMHM i.p. immediately after infection. A further group (treatment control) of infected animals is treated i.p. with various high doses of cefotaxime (contained in 0.5 ml of water) and with physiological saline solution (0.5 ml) immediately after infection.

A fourth group of mice is treated i.p. with various high cefotaxime concentrations (eight animals per cefotaxime concentration; cefotaxime dose as in group 3) and with 50 mg/kg of HMHM immediately after infection.

The number of surviving animals is noted daily over the course of 10 days. Using these numbers, the mean effective dose ($ED_{50\%}$) of cefotaxime, i.e. the cefotaxime dose which must be given in order to ensure the survival of half of the experimental animals, is calculated with the aid of the probit method.

The $ED_{50}$ is used as a parameter for evaluating the chemotherapeutic activity of cefotaxime or of the combinations of cefotaxime with HMHM.

TABLE 1

Chemotherapeutic activity of the combination of cefotaxime (CTX) and 1-(5-hydroxy-5-methylhexyl)-3-methylxanthine (HMHM) in experimental infections in the mouse

| Compound | Treatment (hours after infection) | Mean effective dose ($ED_{50}$ mg/kg) | | |
|---|---|---|---|---|
| | | *S. aureus* Giorgio | *E. coli* 078 | *S. typhimuxium* MX II |
| HMHM, 50 mg/kg | 0 | >50 | >50 | >50 |
| CTX + 0.9% NaCl | 0 | 12.50 | 0.102 | 0.554 |
| CTX + HMHM, 50 mg/kg | 0 | 1.09 | 0.006 | 0.037 |

We claim:

1. A composition containing an effective amount of cefotaxime and at least one xanthine derivative selected from the group consisting of
   1-(5-hydroxyhexyl)-3-methyl-7-propylxanthine,
   3-methyl-1-(5-oxohexyl)-7-propylxanthine,
   7-propyl-1-(5-hydroxy-5-methylhexyl)-3-methylxanthine,
   7-ethoxymethyl-1-(5-hydroxy-5-methylhexyl)-3-methylxanthine, 3-methyl-l-(5-oxohexyl)-7-(2-oxopropyl)-xanthine and
   1-(5-hydroxy-5-methylhexyl)-3-methylxanthine.

2. The composition as claimed in claim 1, wherein the xanthine derivative is 1-(5-hydroxy-5-methylhexyl)-3methylxanthine.

3. The composition as claimed in claim 1, which contains cefotaxime and 1-(5-hydroxy-5-methylhexyl)-3methylxanthine.

4. A pharmaceutical composition comprising the composition as claimed in claim 1 and a pharmaceutically suitable carrier.

5. (Amended) A method for treatment of bacterial infectious diseases comprising administering to a host in need thereof an effective amount of cefotaxime and at least one xanthine derivative selected from the group consisting of
   1-(5-hydroxyhexyl)-3-methyl-7-propylxanthine,
   3-methyl-1-(5-oxohexyl)-7-propylxanthine,
   7-propyl-1-(5-hydroxy-5-methylhexyl)-3-methylxanthine,
   7-ethoxymethyl-1-(5-hydroxy-5-methylhexyl)-3-methylxanthine,
   3-methyl-1-(5-oxohexyl)-7-(2-oxopropyl)-xanthine and
   1-(5-hydroxy-5-methylhexyl)-3-methylxanthine.

6. A method for treatment of septic shock comprising administering to a host in need thereof an effective amount of cefotaxime and at least one xanthine derivative selected from the group consisting of
   1-(5-hydroxyhexyl)-3-methyl-7-propylxanthine,
   3-methyl-1-(5-oxohexyl)-7-propylxanthine,
   7-propyl-1-(5-hydroxy-5-methylhexyl)-3-methylxanthine,
   7-ethoxymethyl-1-(5-hydroxy-5-methylhexyl)-3-methylxanthine,
   3-methyl-1-(5-oxohexyl)-7-(2-oxopropyl)-xanthine and
   1-(5-hydroxy-5-methylhexyl)-3-methylxanthine.

* * * * *